United States Patent [19]

Rumbold et al.

[11] Patent Number: 4,567,770
[45] Date of Patent: Feb. 4, 1986

[54] ULTRASONIC TRANSDUCER APPARATUS AND METHOD FOR HIGH TEMPERATURE MEASUREMENTS

[75] Inventors: John G. Rumbold, Mechanicsville; Jack W. Raisch, Newtown, both of Pa.

[73] Assignee: Sonic Instruments Inc., Trenton, N.J.

[21] Appl. No.: 477,448

[22] Filed: Mar. 21, 1983

[51] Int. Cl.⁴ .................................. G01N 29/00
[52] U.S. Cl. ............................. 73/644; 73/617; 73/624
[58] Field of Search .............. 73/628, 641, 644, 617, 73/624

[56] References Cited

U.S. PATENT DOCUMENTS

| | | | |
|---|---|---|---|
| 2,697,936 | 12/1954 | Farrow | 73/644 |
| 3,242,723 | 3/1966 | Evans | 73/644 |
| 3,320,797 | 5/1967 | Tajiri et al. | 73/644 |
| 3,350,923 | 11/1967 | Cross | 73/617 |
| 3,534,609 | 10/1970 | Grenfell et al. | 73/597 |
| 3,570,305 | 3/1971 | Sasaki | 73/617 |
| 3,625,051 | 12/1971 | Uozumi | 73/644 |
| 3,646,806 | 3/1972 | Yamaguchi et al. | 73/644 |
| 4,014,211 | 3/1977 | Araki et al. | 73/644 |
| 4,182,155 | 1/1980 | Fowler | 73/644 |
| 4,261,197 | 4/1981 | Mansfield | 73/644 |
| 4,375,167 | 3/1983 | Nusbickel, Jr. et al. | 73/644 |
| 4,398,421 | 8/1983 | White | 73/644 |

Primary Examiner—Howard A. Birmiel
Attorney, Agent, or Firm—Sachs & Sachs

[57] ABSTRACT

A non-destructive method and apparatus for inspecting materials in excess of 500° C. includes a dual transducer disposed upon a delay line suitable for operation at the elevated temperatures. The delay line is divided into two parts acoustically isolated and is cooled by a fluid to maintain the surface upon which the transducers are mounted at a safe operating temperature.

7 Claims 10 Drawing Figures

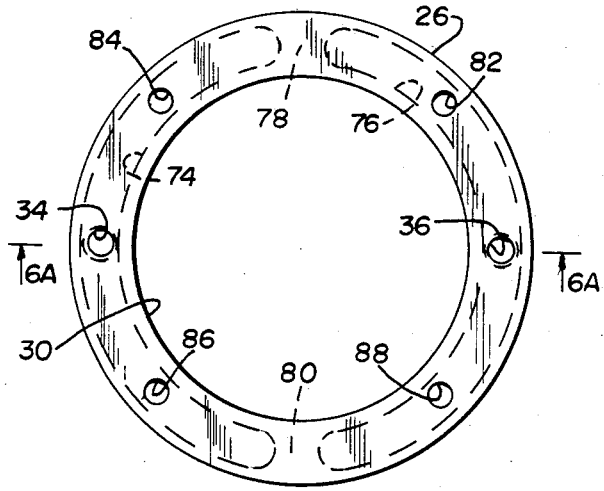
FIGURE 3
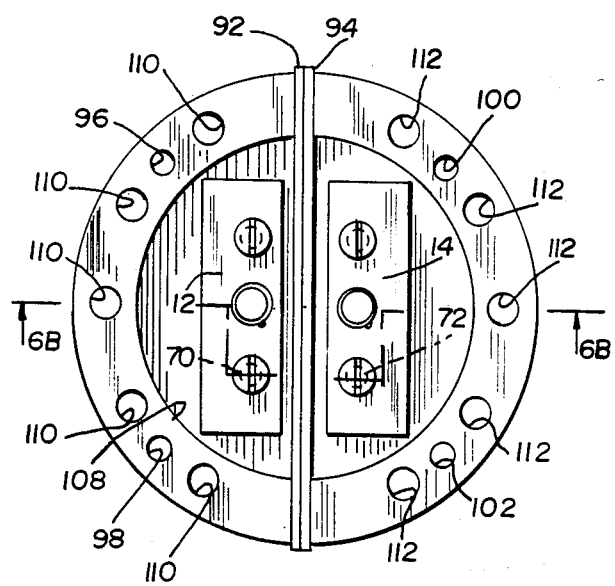
FIGURE 4
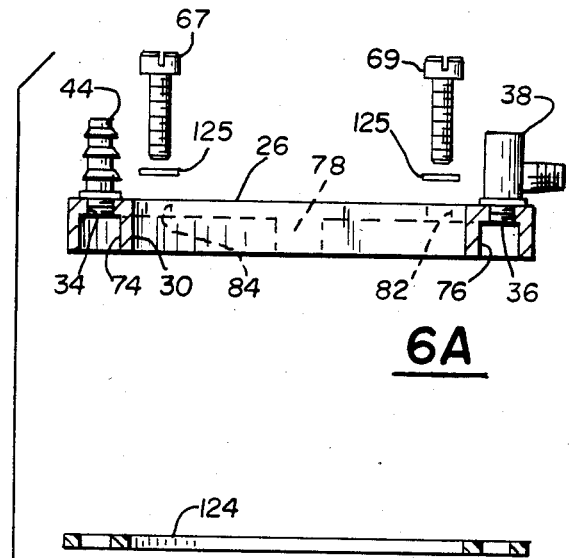
6A
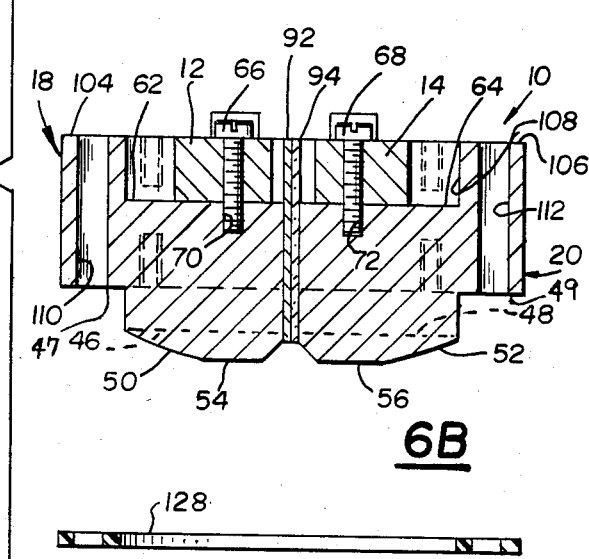
FIGURE 6
6B
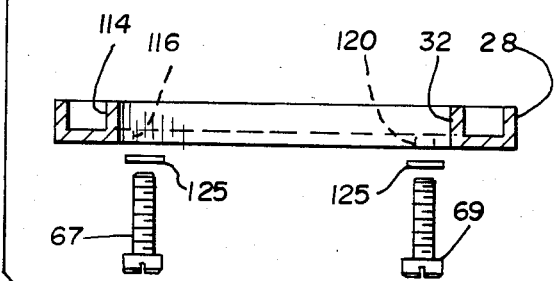
6C

ULTRASONIC TRANSDUCER APPARATUS AND METHOD FOR HIGH TEMPERATURE MEASUREMENTS

BACKGROUND OF THE INVENTION

1. Field of the Invention

The present invention relates to ultrasonic inspection techniques, and in particular relates to a non-destructive method and apparatus for inspecting materials at temperatures in excess of 500° C.

2. Discussion of the Relevant Art

Ultrasonic measurement techniques have been used for many years to measure characteristics of materials and to inspect the materials utilizing a pulse echo method to locate and determine the magnitude of imperfections in the material. Utilizing known techniques, it is also possible to determine the thickness of material under test. However, the measurement of characteristics of materials at temperatures in excess of 500° C. was developed recently. The technique utilized a high pressure dry coupling method to introduce the ultrasonic wave into the heated materials and typically measured the longitudinal and shear acoustic velocity of a material to determine its mechanical properties. The measurement device utilized a single transducer with a metallic delay line that incorporated some type of cooling so that the transducer could be kept within safe operating temperatures. The length of the metallic delay line was a limiting factor which determined the maximum thickness of the material that could be inspected. This is because the second multiple echo from the end of the delay line provides a practical limit beyond which echoes from within the material being tested are obscured. Practical systems utilizing this technique have been designed and they are capable of measuring thicknesses of materials up to about three and one-half inches (3½").

One of the known systems is disclosed in U.S. Pat. No. 3,534,609 issued to H. W. Grenfell, et al on Oct. 20, 1970. The apparatus disclosed in the patent to Grenfell, et al is used to measure the temperature of a metal and requires the use of two delay lines (extension bars) disposed on either side of the material under test and in intimate contact therewith. The opposite ends of the delay lines have the transducers affixed thereon. The extension bars are surrounded by a jacket which has input and output ports designed to carry water for cooling these bars. The technique as disclosed requires that two surfaces of a material under test be contacted by the delay lines (extension bars) and requires that equal pressure be exerted on both bars in order to insure the transmission and reception of the ultrasonic signal into the material under test.

The present invention overcomes the shortcomings found in the art by providing a dual transducer and method which requires contact with only one surface of the material under test and thereby simplifies the measurement and is not limited by requiring access to multiple surfaces.

SUMMARY OF THE INVENTION

Therefore, it is an object of the present invention to provide a simplified method for inspecting materials at temperatures in excess of 500° C. which requires contact with only one surface of the material.

It is another object of the present invention to provide a dual transducer wherein the transducer elements when mounted on a delay line are acoustically isolated.

It is yet another object of the present invention to provide a dual transducer and delay line wherein the cooling utilized for the delay line is an integral part of the delay line.

It is still another object of the present invention to provide a dual transducer which may be utilized at elevated temperatures for inspecting materials above 3½ inches (8.89 cm) thick, which is relatively easy to manufacture and is reliable.

A non-destructive method for inspecting materials at temperatures in excess of 500° C., according to the principles of the present invention, comprises the steps of: providing a dual transducer having a pair of transducer elements; providing a delay line suitable for operation at the elevated temperatures, the delay line is adapted to receive the dual transducer elements and be in intimate sonic contact therewith while providing acoustic isolation therebetween, the delay line is adapted to be in intimate contact with only one surface of the material under test; acoustically coupling the delay line to one surface of the material to be inspected; fluid cooling the delay line to maintain the dual transducer elements in contact therewith at a safe operating temperature; transmitting an ultrasonic wave through one portion of the delay line by one of the dual transducer elements; receiving an acoustical sound wave by the other of the said dual transducer elements reflected from a defect appearing in the material under test or from the far surface of the material through the other portion of the delay line; and providing means for determining the location of the defect relative to the position of the dual transducer on the material.

An apparatus for ultrasonically inspecting materials at a temperature in excess of 500° C. comprises: a delay line having an upper surface and a lower surface divided into two portions, each acoustically isolated from the other; first and second transducer elements disposed, respectively, on the upper surfaces of the delay line portions and acoustically coupled thereto; and cooling means for maintaining the transducer element at a safe operating temperature when the delay line lower surface is in contact with the material to be inspected; an ultrasonic signal generated by the first transducer element traveling through one of the delay line portions and an acoustical echo being received by the second transducer element after being reflected from a defect in the material under test or the far side thereof and traveling through the other of the delay line portions.

The foregoing and other objects and advantages will appear from the description to follow. In the description, references made to the accompanying drawing which forms a part hereof, and in which is shown by way of illustration specific embodiments in which the invention may be practiced. These embodiments will be described in sufficient detail to enable those skilled in the art to practice the invention and it is to be understood that other embodiments may be utilized and that structural changes may be made without departing from the spirit and scope of the invention. The following detailed description is, therefore, not to be taken in a limiting sense, and the scope of the present invention is best defined by the appended claims.

BRIEF DESCRIPTION OF THE DRAWING

In order that the invention may be more fully understood, it will now be described, by way of example, with reference to the accompanying drawing in which:

FIG. 3 is a top plan view of an upper ring member;

FIG. 4 is a top plan view of a delay line with a pair of transducer elements being exposed thereon;

FIG. 6 (A, B, C) is an exploded, cross-sectional view of the apparatus taken along the lines 6A—6A of FIG. 3, 6B—6B of FIG. 4 and 6C—6C of FIG. 5, respectively.

DESCRIPTION OF THE PREFERRED EMBODIMENTS

Figure 1:
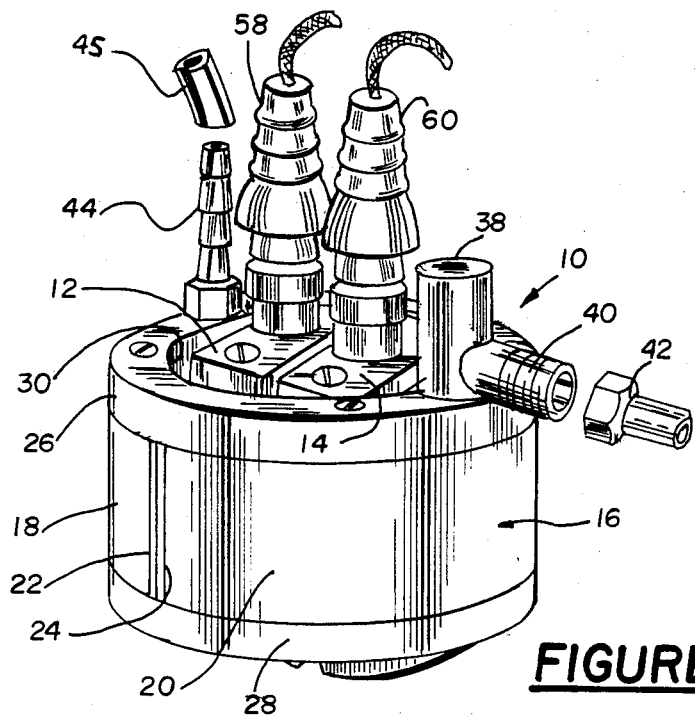
FIG. 1 is a pictorial representation of a dual transducer and delay line apparatus, according to the principles of the present invention.
Figure 2:
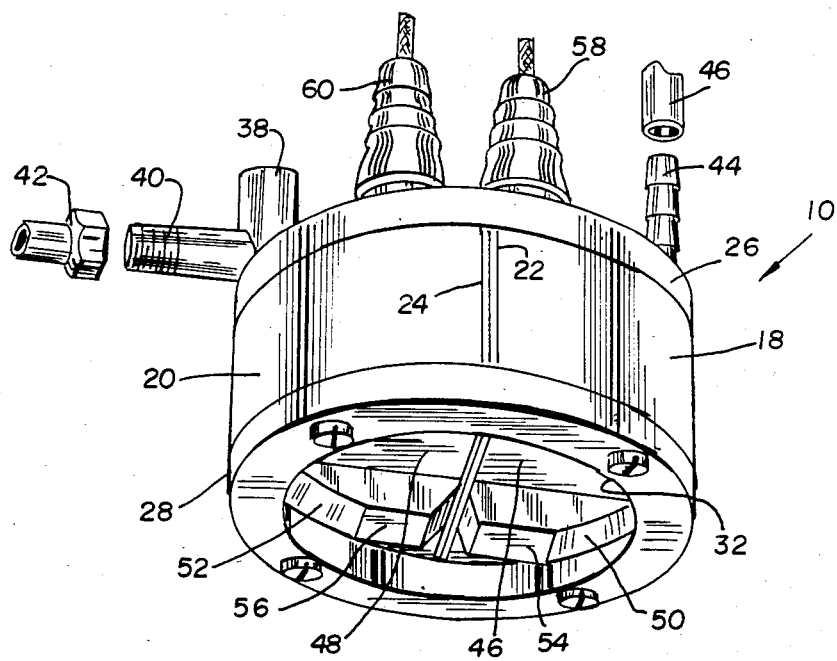
FIG. 2 is a pictorial representation of the apparatus shown in FIG. 1 with the delay line lower surface being exposed for view.

Referring now to the figures and, in particular, to FIGS. 1 and 2 which show a dual transducer apparatus that includes a pair of transducer elements 12 and 14 disposed upon a delay line 16. The delay line 16 includes two solid portions 18 and 20 separated by a metal sheet 22 and an asbestos sheet 24 sandwiched between the solid portions 18 and 20 and held in position by an upper ring member 26 and a lower ring member 28 having apertures 30 and 32, respectively, which receive the solid portions 18 and 20 with the metal and asbestos sheets sandwiched therebetween.

Upper ring member 26 is provided with threaded apertures 34 and 36 (see FIG. 6A). A liquid coupling receptacle 38 is threaded into aperature 36. Receptacle 38 is provided with an outwardly extending threaded portion 40 onto which a fluid connector 42 may be coupled. Fluid output nipple 44 is threaded into aperture 34 and provides an exit port for the fluid which is preferably water or oil (not shown). Nipple 44 is connected to a hose 45 which leads the fluid to another location where it may be cooled for recycling or disposed of.

The lower surface 46 and 48 of the solid portions 18 and 20, respectively, are provided with an outwardly extending portion 50 and 52, respectively. The outwardly extending portions 50 and 52 are provided with a flattened area 54 and 56, respectively, to insure good surface contact with the material under test.

Transducer elements 12 and 14 are connected by means of connector 58 and 60, respectively, and their respective wires to the measuring equipment (not shown). Transducer elements 12 and 14 are mounted to the upper surfaces 62 and 64 by means of pairs of threaded screws 66 and 68, respectively, which are received into threaded apertures 70 and 72 provided in solid portions 18 and 20, respectively (see FIG. 6B).

Referring now to FIG. 3 which shows a top view of the upper ring member 26 that has provided therein a pair of channels 74 and 76 which extend proximate the periphery thereof. The channels are spaced apart by two solid portions 78 and 80. Four spaced apertures 82, 84, 86 and 88 are adapted to receive two pairs of screws 67 and 69 therethrough in order to permit affixing the upper ring 26 to the solid portions 18 and 20 as will be described hereinafter. A centrally disposed aperture or through hole 30 is provided in ring member 26 and it is adapted to receive and provide clearance so that transducer elements 12 and 14 may pass therethrough. A cross-sectional view taken along the line 6A—6A of FIG. 3 is shown in FIG. 6A.

Referring now to FIG. 4 which is a top plan view of the solid portions 18 and 20 of the dual transducer apparatus 10 and FIG. 6B which is a cross-sectional view thereof taken along the line 6B—6B of FIG. 4. The solid portions 18 and 20 are fabricated as a single piece and then cut transversely to provide two halves as shown in FIGS. 4 and 6B. Disposed in the cut-away portion which preferably is approximately 0.1 inches is a sheet of steel 92 and a sheet of asbestos 94. The steel and asbestos sheets 92 and 94, respectively, provide the necessary acoustical isolation between solid portion 18 and solid portion 20. Threaded apertures 96, 98, 100 and 102 are provided on both the top surface 104 and 106 of solid portions 18 and 20, and the bottom surfaces 47 and 49 of solid portions 18 and 20, respectively, and are adapted to receive two pairs of screws 67 and 69 therein to retain the upper and lower ring members 26 and 28 to the solid portions 18 and 20. A flat bore hole 108 is centrally disposed in the solid portion prior to being cut into two halves. The end of bore hole 108 forms the upper surface 62 and 64 of the solid portions 18 and 20 and are ideally suited to receive the transducer elements 12 and 14 thereon by means of the mounting screw pairs 66 and 68. Preferably, a coupling oil or grease is placed on surfaces 62 and 64 prior to the mounting of the transducer elements 12 and 14 thereon. A plurality of through holes 110 and 112 running generally parallel to the longitudinal or vertical axis of the solid portions are provided in the solid portions 18 and 20.

Figure 5:
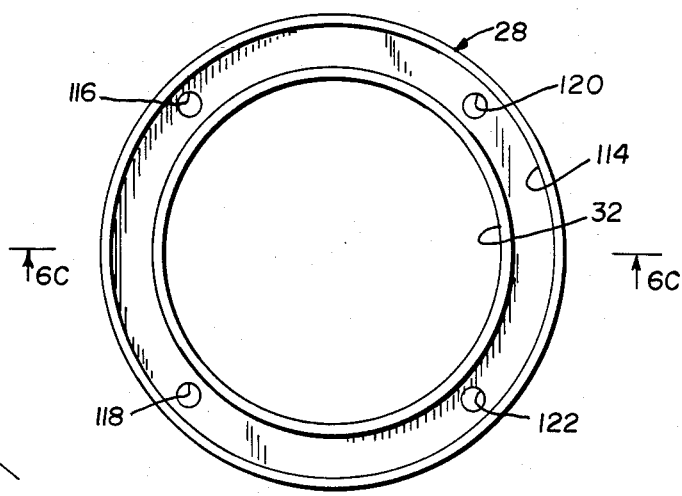
FIG. 5 is a top plan view of the lower ring member.

Referring now to FIGS. 5 and 6C, there is shown a top plan view of the lower ring member 28 which is provided with a peripheral channel 114 which extends completely around the lower ring member 28 and a centrally disposed aperture 32. Lower ring member 28 is also provided with apertures 116, 118, 120 and 122 which are adapted to receive two pairs of screws 67 and 69 therethrough in order to mount or affix lowr ring member 28 to the solid portions 18 and 20, as will be explained hereinafter.

FIG. 6 is an exploded assembly presentation of the dual transducer apparatus 10 showing the method of assembly of the individual elements. Once the elements have been fabricated, they may be assembled by placing upper ring member 26 onto the surface of solid portions 18 and 20 with preferably a fiber gasket 124 disposed therebetween and some sealant such as RTV utilized to hold the fiber gasket in position as the upper member 26 is placed thereon. Screw pairs 67 and 69 are inserted into apertures 82, 84, 86 and 88 utilizing nylon washers 125 and a small amount of RTV to provide a water-tight seal as will become apparent shortly. Lower ring member 28 is then mounted to the lower surface 47 and 49 of the solid portions 18 and 20 with a fiber gasket 128 placed therebetween with some additional RTV placed thereon. Screw pairs 67 and 69 are then inserted into apertures 116, 118, 120 and 122 utilizing a nylon washer 125 under each screw head with small amounts of RTV in order to provide a water-right seal as the screws are tightened to hold down the lower ring member 28 to the solid portions 18 and 20 providing a complete assembly for the delay line 16. Transducer elements 12 and 14 are then mounted to the surfaces 62 and 64, respectively, as indicated earlier, thereby completing the assembly of the two transducer apparatus. Electrical connectors 58 and 60 are then connected to the transducer elements and are utilized to energize one transducer and receive the output signal of the other transducer when it is impinged upon with sonic energy reflected from the material under test.

Figure 7:
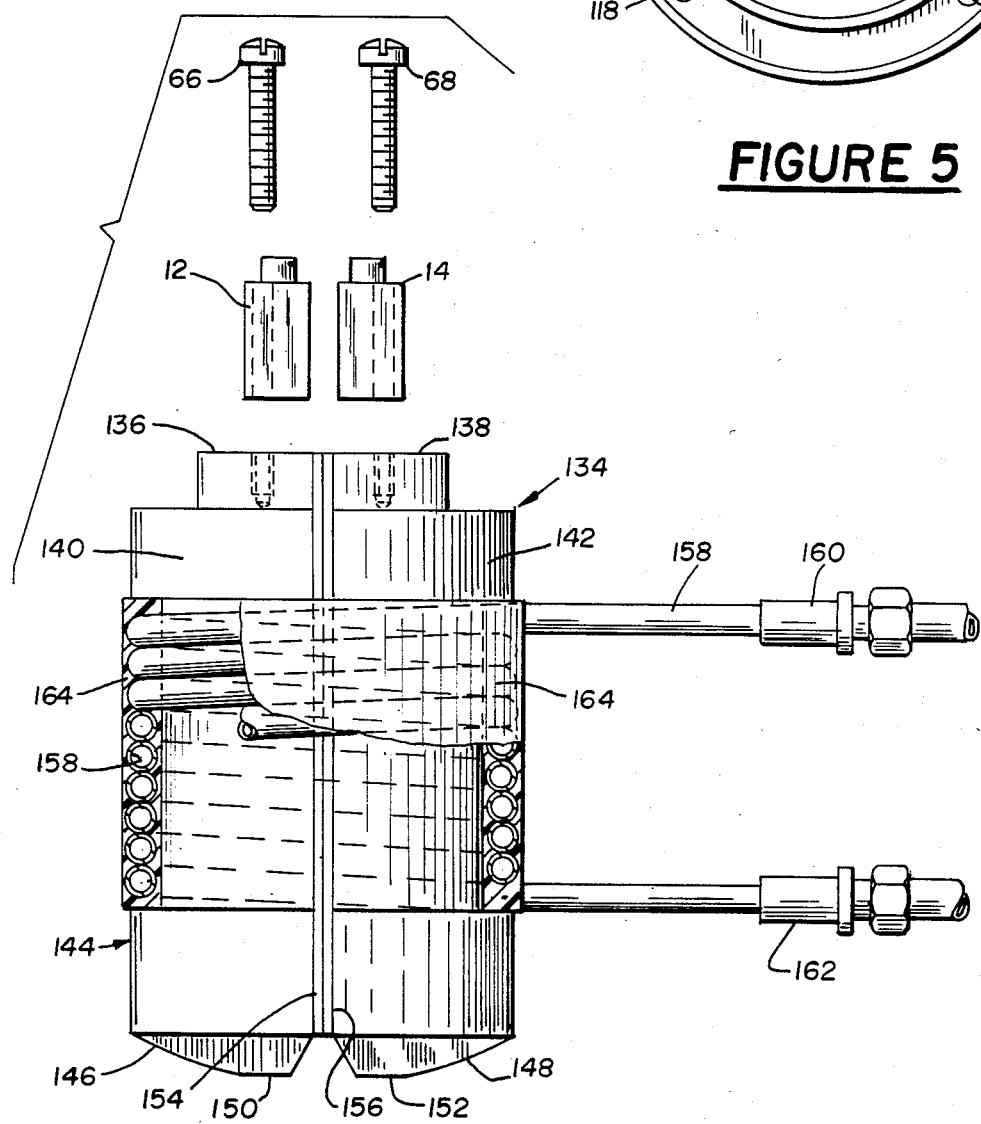

An alternative embodiment of the dual transducer apparatus is shown in FIG. 7. Dual transducer apparatus 134 includes transducer elements 12 and 14 which are affixed to the upper surface 136 and 138 of solid portions 140 and 142, respectively, of delay line 144. The lower surface 146 and 148 is fabricated in the same manner as the embodiment shown in FIG. 2 and is provided with flattened areas 150 and 152 to insure contact with the material under test. The solid portions 140 and 142 have sandwiched therebetween a steel sheet 154 and an asbestos sheet 156 in order to provide acoustic isolation between solid portions 140 and 142. The solid portions 140 and 142 are held in position by a hollow tubular member 158, preferably made of copper which provided with fittings 160 and 162, one on each end, which are adapted to receive a mating fitting through which will be supplied a cooling fluid such as oil or water. The tubing 158 is tightly wound around the solid portions 140 and 142 and held in intimate thermal conductive contact with the solid portions by means of a conductive epoxy 164. Once the epoxy sets, a rigid assembly is accomplished and transducer elements 12 and 14 are mounted in the same manner as discussed with regard to the embodiments shown in FIG. 1.

In operation, the dual transducer element will be placed upon the material under test with any suitable device capable of exerting pressures approaching 8,000 pounds per square inch in order to insure sufficient contact with the test material by the flat surfaces 54 and 56 or 150 and 152 provided on the dual transducer apparatuses. No couplant is required between the flat surfaces and the material under test. Electrical energy is supplied to one transducer in a conventional manner and the echo received by the second transducer will be coupled to the equipment measuring the time element therebetween. Fluid is caused to flow through the copper tubing in a conventional manner in the embodiment shown in FIG. 7 thereby cooling the solid portions 140 and 142 maintaining the surfaces 136 and 138 at a temperature suitable for the operation of transducers 12 and 14. Fluid is coupled through coupling receptable 38 in a conventional manner, with the dual transducer apparatus 10. The fluid will flow down through the through holes 112 provided in the solid portion 20 being dispersed by the channel 76 to each of the holes 112. Once they reach the lower ring member 28, they will circle in channel 114 and exit via through holes 110 to channel 74 where the fluid will be directed out of output nipple 44 where it may be directed to a remote location to be cooled and recirculated back through the input again. It is obvious that by rotating upper ring member 26 ninety degrees, the fluid can be forced to flow into holes 110 and 112 simultaneously and exiting through these apertures simultaneously thereby cooling both transducer elements 12 and 14 at the same time (in parallel rather than series).

Hereinbefore has been disclosed a dual transducer apparatus and method for performing high temperature ultrasonic measurements on material which has a temperature in excess of 500° C. It will be understood that various changes in the details, materials arrangement of parts and operating conditions which have been herein described and illustrated in order to explain the nature of the invention may be made by those skilled in the art within the principles and scope of the invention.

Having thus set forth the nature of the invention, what is claimed is:

1. A non-destructive method for inspecting materials at temperatures in excess of 500° C. comprising the steps of:
   (a) providing a dual transducer having a pair of transducer elements;
   (b) providing a delay line suitable for operation at said temperatures, said delay line being adapted to receive said dual transducer elements and be in intimate sonic contact therewith while providing acoustic isolation therebetween, said delay line being adapted to be in direct intimate contact with only one surface of said material under test;
   (c) acoustically coupling said delay line to one surface of said material to be inspected by direct intimate contact thereto;
   (d) fluid cooling said delay line to maintain said dual transducer elements in contact therewith at a safe operating temperature;
   (e) transmitting an ultrasonic wave through one portion of said delay line by one of said dual transducer elements;
   (f) receiving an acoustical sound wave by the other of said dual transducer elements reflected from a defect appearing in said material under test or from the far surface of said material through the other portion of said delay line; and
   (g) providing means for determining the location of said defect relative to the position of said dual transducer on said material.

2. The method according to claim 1 further including the step of (h) displaying the location of said defect.

3. The method according to claim 1 wherein said fluid cooling is accomplished by water flowing in a continuous path simultaneously cooling both transducer elements of said dual transducer.

4. An apparatus for ultrasonically inspecting materials at a temperature in excess of 500° C. comprising:
   (a) a delay line having an upper surface and a lower surface divided into two portions, each acoustically isolated from the other;
   (b) first and second transducer elements disposed, respectively, on said upper surfaces of said delay line portions and acoustically coupled thereto; and
   (c) cooling means for maintaining said transducer elements at a safe operating temperature when said delay line lower surface is in intimate contact with a surface of said material to be inspected;
   an ultrasonic signal generated by said first transducer element traveling through one of said delay line portions causes an acoustical echo to be received by said second transducer element after being reflected from a defect in said material under test or the far side thereof after traveling through the other of said delay line portions.

5. An apparatus according to claim 4 wherein said cooling means simultaneously cools both said transducer elements.

6. An apparatus according to claim 4 wherein said delay line comprises:
   (a) an upper ring member having;
      (i) two channels disposed proximate the circumference thereof, each of said channels extending less than one half the distance of said circumference leaving solid portions therebetween, (ii) fluid input and output means, said fluid means communicating with one of said two channels and said fluid output means communicating with the other of said two channels, and (iii) a centrally disposed aperture;

(b) a lower ring member having;
  (i) a channel disposed proximate the circumference thereof, said channel extending completely around said ring member, and
  (ii) a centrally disposed aperture;

(c) acoustic isolation means disposed between said delay line two portions sandwiching said acoustic isolation means therebetween and disposed within said upper and lower ring apertures, said delay line portions being provided with through apertures disposed about the periphery of said portions in an axial direction to provide a continuous fluid flow path from said upper ring input means to said upper ring output means via, one of said upper ring channels, the apertures in one of said portions, said lower ring channel, the apertures in the other of said portions, and the other of said upper ring channels.

7. An apparatus according to claim 4 wherein said delay line comprises:

(a) a solid member cut in half along its longitudinal axis to form said two portions;

(b) acoustical isolation means disposed between said two portions; and (c) a hollow cooling coil adapted to receive cooling liquid therethrough, said cooling coil circumscribing said delay line half portions with said acoustical means disposed therebetween and in intimate contact therewith.

* * * * *